US00PP18246P3

(12) United States Plant Patent
Moore

(10) Patent No.: US PP18,246 P3
(45) Date of Patent: Nov. 27, 2007

(54) RASPBERRY CULTIVAR 'CASCADE BOUNTY'

(50) Latin Name: ***Rubus ideaus* L.**
Varietal Denomination: Cascade Bounty

(75) Inventor: Patrick P. Moore, Puyallup, WA (US)

(73) Assignee: Washington State University Research Foundation, Pullman, WA (US)

( * ) Notice: Subject to any disclaimer, the term of this patent is extended or adjusted under 35 U.S.C. 154(b) by 4 days.

(21) Appl. No.: 11/057,898

(22) Filed: Feb. 15, 2005

(65) Prior Publication Data

US 2006/0185042 P1 Aug. 17, 2006

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
(74) *Attorney, Agent, or Firm*—Steven J. Adamson

(57) ABSTRACT

A new and distinct cultivar of raspberry (i.e., *Rubus idaeus* L.). The cultivar forms medium sized, medium colored, tart flavored fruit. The fruit is round in shape with similar length and width. Based on trials on root rot infested soil, the cultivar appears to be highly tolerant of root rot, producing very high yields on these sites.

5 Drawing Sheets

GOVERNMENT INTERESTS

The invention was made in part with Federal formula funds pursuant to the Hatch Act and was part of Project WNP00640. The United States Government has certain rights in the invention.

FIELD OF THE INVENTION

This invention relates to a new and distinct cultivar of raspberry plant with a botanical name of *Rubus ideaus* L., and the cultivar designation 'Cascade Bounty'.

BACKGROUND OF THE INVENTION

Many cultivars of raspberry plant are known. For instance, raspberry cultivars named 'Lauren', 'Encore', 'Prelude,' and 'WSU 1090' are described in U.S. Plant Pat. Nos. 10,610, 11,746, 11,747, and 14,522 respectively. The parents of the new and distinct cultivar of the present invention are 'Chief' and WSU 984.

The instant plant, Cascade Bounty, originated from a hand-pollinated cross of WSU 984 (non-patented), the female parent, × 'Chief" (non-patented), the male parent, made in 1992 at Washington State University Puyallup Research and Extension Center, Puyallup Wash. 'Chief' is a red raspberry cultivar released from the University of Minnesota in 1930. 'Chief' produces round, small to medium fruit that ripens early in the season. 'Chief' is highly root rot tolerant and very winter hardy. WSU 984 is a red raspberry selection from the Washington State University breeding program. WSU 984 was highly productive, has long fruiting laterals and produces long conic light colored fruit.

SUMMARY OF THE INVENTION

'Cascade Bounty' is distinguished primarily by its high productivity and high level of tolerance to root rot. The fruit is rounded in shape and tart.

'Cascade Bounty' is distinguished from its parent WSU 984 by having more rounded fruit, darker fruit color and more acidic fruit.

'Cascade Bounty' is distinguished from its parent 'Chief' in having larger leaves with terminal, distal lateral and basal lateral leaflets all being longer and wider than Chief. 'Cascade Bounty' has larger fruit, more drupelets per fruit, greater drupelet weight, larger seeds, later harvest season and greater productivity than 'Chief'.

'Boyne' (non-patented) and 'Killarney' (non-patented) are red raspberry cultivars that also have 'Chief' as one of their parents. 'Cascade Bounty' is distinguished from 'Boyne' by a longer petiole, greater length of terminal and basal lateral leaflets and sessile basal lateral leaflets for primocane leaves, larger fruit, more drupelets per fruit, larger drupelets, larger individual seed weight, lighter fruit color and a later harvest season. 'Cascade Bounty' is distinguished from 'Killarney' by a longer petiole, longer leaflets and sessile basal lateral leaflets for primocane leaves, larger fruit, more drupelets per fruit, larger drupelets, larger individual seed weight, and a later harvest season.

'Cascade Bounty' is distinguished from 'Meeker' (non-patented) in having sessile basal lateral leaflets, shorter and narrower basal lateral leaflets for primocane leaves, fewer drupelets per fruit, larger drupelets, larger seeds, more acidic fruit, more fruit per lateral, more fruit per fruiting node, and greater tolerance to root rot.

'Cascade Bounty' is distinguished from 'Cascade Delight' (patented as WSU 1090, U.S. Plant Pat. No. 14,522) by in having sessile basal lateral leaflets, smaller leaflets on primocanes, lighter colored spines on the primocanes, greater total number of buds, flowers and developing fruit per lateral, node and fruiting nodes, greater number of fruit per lateral and fruit per fruiting node, smaller length to width ratio of fruit, fewer drupelets per fruit, smaller drupelets, smaller fruit, and greater tolerance to root rot.

'Cascade Bounty' is distinguished from 'Chilliwack' (non-patented), 'Comox' (non-patented), 'Cowichan' (non-patented, 'Encore' (U.S. Plant Pat. No. 11,747), 'Malahat' (non-patented), 'Tulameen' (non-patented), and 'Qualicum'

(non-patented) by having greater tolerance to root rot in a replicated yield planting on a site with severe root rot. 'Cascade Bounty' was very vigorous, while most or all of the plants of these cultivars died on this site.

BRIEF DESCRIPTION OF THE DRAWINGS

The accompanying photographs show typical specimens of the new cultivar, in color as nearly true as it is reasonably possible to make in color illustrations of this character. Photographs are intended to show morphological features of the plant.

FIG. 1 is a picture of the plant of 'Cascade Bounty', showing the growth habit of the plant, taken Jun. 23, 2004.

FIG. 2 is a photograph of a winter cane of 'Cascade Bounty', taken Feb. 3, 2004. The waxy bloom is rubbed off in one portion of the cane.

FIG. 3 is a photograph of a young primocane of 'Cascade Bounty', less than 30 cm tall grown in a greenhouse, taken Sep. 27, 2004, showing frequency and shape of spines.

FIG. 4 is a photograph of the upper surface of a leaf from a primocane of 'Cascade Bounty' taken Jun. 17, 2003.

FIG. 5 is a photograph of fruit and receptacle of 'Cascade Bounty', taken Jul. 7, 2004.

DETAILED DESCRIPTION

History and Growth

The seeds resulting from the controlled hybridization of 'Chief'×WSU 984 were germinated in a greenhouse during the winter of 1992–1993. Resulting seedlings were planted in the spring of 1993 at Puyallup, Wash. The seedlings fruited in 1995 and one, designated WSU 1162, was selected for its vigor on a poor site, bright uniform sized fruit, and apparent productivity.

During 1995–1996, the original plant selection was propagated asexually in a greenhouse at Puyallup, Wash., by rooting cuttings derived from root material. A replicated planting of four replications of three plants each was established in spring 1996 at Puyallup, Wash. Subsequently, additional test plantings were established from asexually propagated plants that were propagated from root cuttings or micropropagated using meristem cultures from axillary buds of primocanes. Plantings were established in Puyallup and Burlington, Wash. All asexually propagated plants have been observed to be true to type during all asexual multiplication and the vegetative and fruit characteristics of the original plants have been maintained. Plants fruited in the second or third season of growth after planting.

Test plantings have shown this new variety to be adapted to all tested locations in western Washington. There has been no observed winter damage, but winter hardiness is unknown. Plants of the new variety have vigorous growth with long fruiting laterals.

Measurements

When objects could be accurately measured with an 8 mm diameter measuring opening (leaves and fruit), color was measured with a Minolta Chroma Meter CR-200b, which measure color in L*, a*, b* color coordinates. Calibration was performed using a standard white plate supplied by the manufacturer. These L*, a*, b* coordinates were converted and presented in Munsell color notation. For all the other color measurements, color was compared with Royal Horticultural Society Colour Chart color plates and presented as Royal Horticultural Society Colour Chart designations.

The descriptions reported herein are from specimens grown at Puyallup, Wash., unless otherwise noted.

Size

The number of canes per hill, diameter, cane length, number of nodes, internode length, and color are given in comparison to 'Meeker' and 'Cascade Delight' in Table 1. The planting with 'Cascade Bounty' and 'Cascade Delight' were planted in 2000. This site is highly infested with root rot and over 65% of the cultivars and selections in the planting dying from root rot within 4 years. 'Cascade Delight' has some tolerance to root rot and was vigorous, 'Meeker' is susceptible to root rot and had collapsed by 2004. Data for 'Meeker' was collected from an adjacent planting established in 2001, where plants of 'Meeker' had not collapsed. Even in the 2000 planting, 'Cascade Bounty' produced many canes and was very vigorous (FIG. 1). Plants have been grown in the hill system with 10–12 canes retained per hill and the primocanes pruned to 1.2 m in winter. The following summer, fruiting plots were 175 cm tall with a width of 130 cm.

Canes

Primocane emergence was similar for 'Cascade Bounty' and 'Cascade Delight' and occurred approximately Mar. 15, 2004. Bud break for 'Cascade Bounty' and for 'Cascade Delight' was Feb. 23, 2004. When the floricanes were observed Mar. 17, 2003 there were high levels of waxy bloom on the canes making the canes appear Greyed Purple group (186A). The color of the canes depended on the amount of wax on the canes. When the wax was rubbed off the color of the canes was Greyed Orange group (166B). The color of the bud scales were Greyed Purple group (183A). The midwinter color of canes is shown in FIG. 2. In midsummer (Jul. 16, 2004) the cane color was much greener, Yellow-Green Group (145B). At about 30 cm in height the canes had 20–40 spines per cm of cane (FIG. 3). The distal portion of taller canes have fewer spines, smaller spines and the pigmentation at the basal spot and lower portions of the spine decrease. The spine color is Greyed-Purple Group (186A). The spines are straight and pointed toward the base of the canes. There are pigmented spots at the base of the spine that are the same color as the spines. The spine color is similar to 'Meeker' and not as dark as 'Cascade Delight'. The spines at 30 cm of a plant grown in the greenhouse measured Sep. 27, 2004 were 2.4 mm long and the basal spot at the base of the spine was 0.9 mm. The canes are glabrous.

Leaves

The upper surface of the leaves is glabrous with some pubescence at the leaf margin. The leaves are pubescent on the lower surface. The leaflets are generally flat in cross-section. The petioles are pubescent and also have spines that are similar (but smaller) to those on the canes.

Characteristics of primocane leaves are given in Table 2. The petioles of 'Cascade Bounty' are longer than 'Boyne', 'Chief' and 'Killarney'. The length of the terminal leaflet and basal lateral leaflet of 'Boyne' were less than 'Cascade Bounty'. The leaves of 'Cascade Delight' are larger than 'Cascade Bounty', the length and width of the terminal, distal lateral and width of the basal lateral leaflets. The leaves of 'Chief' are smaller than 'Cascade Bounty', the length and width of all leaflets. The leaflets of 'Killarney' were shorter than the leaflets of 'Cascade Bounty'. The leaves of 'Meeker' were generally similar is size to 'Cascade Bounty', except the basal lateral leaflets of 'Meeker' were shorter and narrower than 'Cascade Bounty'.

The primocane leaves of 'Cascade Bounty' are pinnately compound with 5 leaflets (FIG. 4). The leaves have 2 stipules. The distal lateral leaflets and the terminal leaflet overlap slightly. The leaflets are doubly serrated. The leaflets are generally ovate. The tips of all leaflets are acuminate to acute. The base of the terminal leaflet is rounded to cordate. The basal lateral leaflets are sessile and the bases are rounded and relatively symmetrical. The distal lateral leaflets are sessile with asymmetrical leaf bases.

Characteristics of floricane leaves are given in Table 3. There were few differences among cultivars for floricane leaf measurements. The basal lateral leaflets for 'Cascade Bounty' and 'Chief' were sessile, while 'Boyne', 'Cascade Delight', 'Killarney' and 'Meeker' had petioles over 1 mm. The floricane leaves have 3 leaflets that do not overlap. The leaves have 3 leaflets and 2 stipules. The leaflets are generally ovate. The leaflet tips are acuminate to acute. The leaf bases for the terminal leaflet is cordate and the lateral leaflets are rounded.

Flowers and fruit

Fruit of this variety ripens late in the season, with the midpoint of harvest averaging July 12 and the length of the fruiting season averaging 27 days at Puyallup, Wash. The midpoint of harvest for 'Meeker' averaged July 13 with 23.5 days for the length of the fruiting season. Fruit production has not been observed on primocanes. Fruit releases easily from the receptacle. The fruit is medium sized, averaging 3.4 over the season. Early in the fruiting season, fruit was much larger, averaging 5.29 g on Jun. 25, 2004.

Although variable from year to year and among locations, May 6, 2004 was the date for the first open flowers of 'Cascade Bounty' at Puyallup, Wash., the same as for 'Cascade Delight'. The lateral length, number of nodes, number of flowers, flower diameter and color are given in Table 4. 'Cascade Bounty' had a greater total number of buds, flowers and developing fruit per lateral, node, and fruiting node than 'Cascade Delight'. Flower morphology is typical of most red raspberry cultivars and is not useful to identify 'Cascade Bounty'. The petals are White Group (155A), sepals Yellow-Green Group (147C) and pedicels Greyed-Purple Group (184A). The flowers are perfect with generally 5 sepals, 5 petals and numerous stamens (approximately 90, same as 'Cascade Delight') and pistils (approximately 85 based on the number of developed drupelets). The flowers are self-fertile. The flowering trusses are cymose in elongate clusters and at each node on the fruiting lateral the flowers are predominantly borne singly, or sometimes in clusters of two or more. The flowers have no discernable fragrance. The pedicel length, number of fruit and number of fruiting nodes are given in Table 5. The pedicel length was similar in 'Cascade Bounty', 'Cascade Delight' and 'Meeker'. 'Cascade Bounty' had more fruit per lateral and number of fruit per fruiting node than 'Cascade Delight' and 'Meeker'. Differences between the number of flowers (Table 4) and number of fruit (Table 5) are within sampling errors.

Fruit morphological characteristics are given in Table 6. Fruit is round in shape and glossy (FIG. 5). The width of the fruit of 'Boyne' and 'Chief' was greater than their length. The length of the fruit of 'Cascade Delight' was greater than its width. The length and width of the fruit were similar for 'Cascade Bounty' and 'Killarney' and 'Meeker'. The number of drupelets per fruit for 'Cascade Bounty' was less than for 'Cascade Delight' and 'Meeker' and more than 'Boyne', 'Chief' and 'Killarney'. The drupelet weight of 'Cascade Bounty' was less than 'Cascade Delight' but greater than 'Boyne', 'Chief', 'Killarney' and 'Meeker'. The individual seed weight of 'Cascade Bounty' was greater than the five cultivars it was compared with. Fruit of WSU 984 (one of the parents of 'Cascade Bounty') is not available, but in 1994, the shape of its fruit was conic to long conic with the length/width ratio of 1.4 (range 1.2 to 1.6). This is much greater than the length/width ratio of 1.07 for 'Cascade Bounty'. The Munsell color value for fruit of WSU 984 in a 1994 sample was 6R3/6. This is much lighter than 'Cascade Bounty'.

Fruit of 'Cascade Bounty' is tart, but with a good raspberry flavor. The pH, titratable acidity, soluble solids and anthocyanin concentration of processing ripe fruit are given in Table 7. Soluble solids content and pH of 'Cascade Bounty' fruit did not differ from 'Willamette'. The titratable aciditiy of 'Cascade Bounty' did not differ from 'Cascade Delight'. The anthocyanin content of 'Cascade Bounty' fruit did not differ from 'Meeker'. Although not analyzed in 2004, the fruit of WSU 984 (one of the parents of 'Cascade Bounty') was included in analyses in 1992. The anthocyanin concentration for WSU 984 was low, 56% of the value of 'Meeker' fruit harvested that same year in the same planting. In the 2003 comparison, the anthocyanin concentration of 'Cascade Bounty' was over 90% of the value of 'Meeker'.

Because of the fruit acidity, size and firmness, 'Cascade Bounty' probably is not well suited to fresh market use. Therefore, fruit of 'Cascade Bounty' were not evaluated for post-harvest storage.

Fruit production was measured in two plantings replicated plots at Puyallup that were hand harvested. Both plantings were on sites with high levels of root rot. In the planting established in 1996, 'Cascade Bounty' was compared to 'Comox', 'Encore', 'Malahat', 'Meeker', 'Tulameen' and 'Willamette' (Table 8). 'Cascade Bounty' had the highest yield in 1998 and in 1999, but because of root rot in the plots, there was considerable variability among plots. By 1999, all plots of 'Encore' and 'Malahat' had died. In the planting established in 2000, 'Cascade Bounty' was compared to 'Cascade Delight', 'Meeker', 'Chilliwack', 'Willamette', 'Cowichan', 'Malahat', 'Qualicum' and 'Tulameen'. Before the 2003 harvests, all plots of 'Cowichan', 'Malahat', 'Qualicum' and 'Tulameen' had died from root rot. In both 2003 and 2004, yield for these plots was set to 0 and missing values for other variables. 'Cascade Bounty' was extremely productive and had higher yields than all other cultivars in each year. Fruit weight of 'Cascade Bounty' was similar to 'Meeker' in both plantings and both were smaller than 'Cascade Delight'. Fruit firmness for 'Cascade Bounty' was similar to 'Meeker' in both years. The 5%, 50% and 95% harvest dates were similar for 'Cascade Bounty' and 'Cascade Delight' and 'Meeker' (except for the date of 95% of harvest in 2003 for 'Meeker'). 'Cascade Bounty' was also subjectively evaluated in plots established in 2003 that were machine harvested at Burlington, Wash. 'Cascade Bounty' machine harvested acceptably for bulk frozen, puree or juice uses. There was some broken fruit and soft fruit, so it may not be suitable for IQF fruit (Individually Quick Frozen fruit).

Disease resistance

'Cascade Bounty' is susceptible to the large raspberry aphid (*Amphorophora agathonica*) the vector for the mosaic virus complex. It appears to be susceptible to raspberry bushy dwarf virus (RBDV) via pollen transmission. In unsprayed plots, the canes had some spur blight (*Didymella applanata* [Niessl] Sacc.) infections, but with a low incidence. 'Cascade Bounty' has been planted in areas with high levels of root rot (*Phytophthora fragariae* var. *rubi,* Wilcox & Duncan) and has had high yields with vigorous plants. 'Cascade Bounty' appears to have high levels of root rot tolerance.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

TABLE 1

Cane measurements taken on Jul. 16, 2004, Puyallup, Wash..

| | CASCADE BOUNTY | Cascade Delight | Meeker |
|---|---|---|---|
| Primocanes | | | |
| Diameter base (mm) | 12.4a | 12.7a | 11.9a |
| Diameter 4 ft (mm) | 8.5a | 8.7a | 10.6a |
| Length (cm) | 187.1a | 191.3a | 212.5a |
| Number of nodes | 37.0a | 35.0a | 44.3a |
| Internode length (cm) | 68.7a | 68.7a | 65.3a |
| Number of canes/hill | 60.0a | 39.7b | 19.0c |
| Cane color | 145B | 145C | 145D |
| Spine color | 186A | 187A | 186A |
| Floricanes | | | |
| Diameter base (mm) | 13.9a | 14.7a | 12.4a |
| Diameter 4 ft (mm) | 11.0a | 10.8a | 7.4b |
| Length (cm) | 189.7a | 193.9a | 143.1b |
| Number of nodes | 22.7b | 24.3b | 30.7a |
| Internode length (cm) | 82.2a | 71.3ab | 48.9b |
| Cane color | 175C | 166C | 165B |

Three canes were measured for each clone.
[z]Royal Horticultural Society Colour Chart designations
Means within a row followed by the same letter are not significantly different at P ≦ 0.05, by Duncan's Multiple Range Test.

TABLE 2

Primocane leaves measured at 4 feet on Jun. 19, 2003, Puyallup, Wash..

| | CASCADE BOUNTY | Boyne | Cascade Delight | Chief |
|---|---|---|---|---|
| Petiole length (mm) | 96.8a | 65.1b | 85.7a | 58.0b |
| Rachis length (mm) | 49.5ab | 48.2b | 58.6a | 47.6b |
| stipule length (mm) | 10.0a | 11.2a | 6.0c | 8.8ab |
| terminal leaflet | | | | |
| length (mm) | 129.5b | 112.0c | 143.8a | 86.9d |
| width (mm) | 83.5b | 79.5b | 101.4a | 60.4c |
| petiolule length (mm) | 16.6bc | 20.5b | 28.7a | 11.8c |
| distal lateral leaflet | | | | |
| length (mm) | 100.1b | 94.2b | 116.1a | 70.3c |
| width (mm) | 53.7b | 55.6b | 64.7a | 41.8c |
| petiolule length (mm) | 0.0a | 0.0a | 0.0a | 0.0a |
| basal lateral leaflet | | | | |
| length (mm) | 124.9a | 108.4b | 135.4a | 85.3c |
| width (mm) | 78.1b | 73.6bc | 88.0a | 61.3d |
| petiolule length (mm) | 0.0d | 2.6c | 3.6b | 0.0d |
| Color | | | | |
| upper surface of leaflet | | | | |
| Munsell Color | 6.5GY3/3 | 6.5GY3/3 | 6.5GY4/3 | 6.5GY3/3 |
| lower surface of leaflet | | | | |
| Munsell Color | 6.5GY5/2 | 6GY5/2 | 6GY5/2 | 6GY5/2 |

TABLE 2-continued

Primocane leaves measured at 4 feet on Jun. 19, 2003, Puyallup, Wash..

| | Killarney | Meeker |
|---|---|---|
| Petiole length (mm) | 57.4b | 94.3a |
| Rachis length (mm) | 42.3ab | 53.6ab |
| stipule length (mm) | 7.1bc | 11.4a |
| terminal leaflet | | |
| length (mm) | 98.2d | 124.2bc |
| width (mm) | 104.7a | 74.8b |
| petiolule length (mm) | 32.4a | 14.2bc |
| distal lateral leaflet | | |
| length (mm) | 82.0bc | 90.6b |
| width (mm) | 56.5b | 43.1c |
| petiolule length (mm) | 0.0a | 0.0a |
| basal lateral leaflet | | |
| length (mm) | 84.1c | 109.2bc |
| width (mm) | 69.4cd | 68.4cd |
| petiolule length (mm) | 0.0d | 5.0a |
| Color | | |
| upper surface of leaflet | | |
| Munsell Color | 6.5GY3/3 | 6.5GY3/3 |
| lower surface of leaflet | | |
| Munsell Color | 6GY6/2 | 6.5GY5/2 |

Five leaves were measured for each clone. All clones had 5 leaflets, except Killarney, which had 1 leaf with 5 leaflets and 4 leaves with 3 leaflets.
Means within a row followed by the same letter are not significantly different at P ≦ 0.05, by Duncan's Multiple Range Test.

TABLE 3

Floricane leaves measured at 4 feet on Jun. 17, 2004, Puyallup, Wash..

| | CASCADE BOUNTY | Boyne | Cascade Delight | Chief |
|---|---|---|---|---|
| Number of leaflets | 3a | 3a | 3a | 3a |
| Petiole length (mm) | 29.6b | 31.9a-c | 39.0ab | 50.4a |
| stipule length (mm) | 1.7a | 0.0a | 0.0a | 0.9a |
| terminal leaflet | | | | |
| length (mm) | 88.4 | 96.5 | 94.3 | 66.6 |
| width (mm) | 65.2a | 55.3a | 68.7a | 51.0a |
| petiolule length (mm) | 15.8a | 14.9a | 27.0a | 13.1a |
| basal lateral leaflet | | | | |
| length (mm) | 64.2b-c | 84.2a | 78.0ab | 58.8cd |
| width (mm) | 40.2a | 47.4a | 43.7a | 40.5a |
| petiolule length (mm) | 0.0b-c | 1.5a | 2.3a | 0.0b |
| Color | | | | |
| upper surface of leaflet | | | | |
| Munsell Color | 5.5GY3/3 | 6GY3/3 | 5GY3/3 | 5GY3/3 |
| lower surface of leaflet | | | | |
| Munsell Color | 5GY6/2 | 5GY5/2 | 4.5GY6/2 | 4GY6/2 |

| | Killarney | Meeker |
|---|---|---|
| Number of leaflets | 3a | 3a |
| Petiole length (mm) | 24.2c | 41.1ab |
| stipule length (mm) | 0.0a | 1.9a |
| terminal leaflet | | |
| length (mm) | 74.8 | 85.1 |
| width (mm) | 60.5a | 57.7a |
| petiolule length (mm) | 16.0a | 19.3a |
| basal lateral leaflet | | |
| length (mm) | 53.8d | 70.2a-c |
| width (mm) | 41.8a | 40.0a |
| petiolule length (mm) | 1.8a | 1.8a |

TABLE 3-continued

Floricane leaves measured at 4 feet on Jun. 17, 2004, Puyallup, Wash..

| | | |
|---|---|---|
| Color | | |
| upper surface of leaflet | | |
| Munsell Color | 5GY3/2 | 6GY3/3 |
| lower surface of leaflet | | |
| Munsell Color | 5.5GY6/2 | 5.5GY6/2 |

Five leaves were measured for each clone.
Means within a row followed by the same letter are not significantly different at P ≦ 0.05, by Duncan's Multiple Range Test.

TABLE 4

Flower measurements taken at 4 feet on May 26, 2004, Puyallup, Wash.

| | CASCADE BOUNTY | Cascade Delight |
|---|---|---|
| Flower diameter | | |
| Sepal-sepal (mm) | 24.2a | 25.5a |
| petal-petal (mm) | 10.2a | 10.6a |
| lateral length (cm) | 594a | 610a |
| Number of nodes/lateral | 13.8a | 15.0a |
| Number of flowering nodes/lateral | 10.0a | 8.5a |
| Number of nodes with more than 1 flower | 9.5a | 6.8b |
| Number of flower buds/lateral | 19.3a | 12.5a |
| Number of flowers/lateral | 5.75a | 3.75a |
| Number of developing fruit/lateral | 6.75a | 1.00b |
| Number of buds, flowers, fruit/lateral | 31.75a | 17.25b |
| Number of buds, flowers, fruit/node | 3.21a | 2.02b |
| Number of buds, flowers, fruit/fruiting node | 2.32a | 1.15b |
| Color[z] | | |
| petals | 155C | 155C |
| sepals | 147D | 147D |
| pedicels[y] | 144A/183A | 144A/183A |

Five flowering laterals were measured for each clone.
[z]Royal Horticultural Society Colour Chart designations
[y]Pedicels were variable in color, being green with exposed portions being red/purple.
Means within a row followed by the same letter are not significantly different at P ≦ 0.05, by Duncan's Multiple Range Test.

TABLE 5

Lateral measurements taken at 4 feet on Jul. 16, 2004, Puyallup, Wash..

| | CASCADE BOUNTY | Cascade Delight | Meeker |
|---|---|---|---|
| Pedicel length (cm) | 14.1a | 24.8a | 19.8a |
| Number of fruit/lateral | 29.0a | 15.0b | 20.0b |
| Number of nodes/lateral | 11.7a | 13.7a | 13.7a |
| Number of fruiting nodes/lateral | 9.0a | 9.7a | 8.7a |
| Number of fruit/fruiting node | 3.2a | 1.5c | 2.3b |

Three fruiting laterals were measured for each clone.
Means within a row followed by the same letter are not significantly different at P < 0.05, by Duncan's Multiple Range Test.

TABLE 6

Fruit morphological characteristics, fruit harvested Jun. 18 and 25, 2004, Puyallup, Wash..

| | CASCADE BOUNTY | Boyne | Cascade Delight | Chief |
|---|---|---|---|---|
| Fruit weight (g) | 5.29b | 2.94e | 7.08a | 1.64f |
| Length (mm) | 23.4b | 17.3d | 30.5a | 14.3e |
| Width (mm) | 22.0a | 19.2b | 22.6a | 15.6c |
| L/W ratio | 1.07b | 0.91c | 1.35a | 0.92c |
| Receptacle diameter (mm) | 8.3b | 6.7c | 9.9a | 5.0d |
| Receptacle length (mm) | 12.7b | 8.1d | 20.0a | 6.2e |
| Drupelet length (mm) | 5.6a | 5.5a | 5.9a | 5.2a |
| Drupelet width (mm) | 4.0bc | 4.1bc | 4.7a | 3.9bc |
| Number of drupelets | 85.8b | 60.6cd | 100.8a | 52.8d |
| Drupelet weight (mg) | 61.8b | 48.9d | 70.2a | 31.1e |
| Total seed weight (mg) | 186.6a | 97.2b | 192.3a | 73.7c |
| Individual seed weight (mg) | 2.18a | 1.60c | 1.91b | 1.40d |
| Munsell Color | 4.5R3/6 | 3.5R3/4 | 4.5R3/6 | 4.5R3/6 |

| | Killarney | Meeker |
|---|---|---|
| Fruit weight (g) | 3.67d | 4.51c |
| Length (mm) | 21.2c | 21.8c |
| Width (mm) | 21.2a | 21.9a |
| L/W ratio | 1.00b | 1.00b |
| Receptacle diameter (mm) | 8.5b | 9.5a |
| Receptacle length (mm) | 10.8c | 13.1b |
| Drupelet length (mm) | 5.6a | 5.6a |
| Drupelet width (mm) | 4.3ab | 3.7c |
| Number of drupelets | 67.6c | 101.8a |
| Drupelet weight (mg) | 54.7c | 44.3d |
| Total seed weight (mg) | 112.5b | 198.5a |
| Individual seed weight (mg) | 1.67c | 1.95b |
| Munsell Color | 4.5R3/6 | 4.5R3/6 |

Boyne, Chief and Killarney harvested on June 18 and Cascade Delight, Meeker and CASCADE BOUNTY harvested on June 25.
Means within a row followed by the same letter are not significantly different at P ≦ 0.05, by Duncan's Multiple Range Test.

TABLE 7

Fruit analysis of red ripe fruit harvested July 2003, at Puyallup, Wash..

| Clone | Soluble solids (° brix) | pH | Titratable acidity (% citric acid) | Anthocyanin Concentration (mg/g fruit) |
|---|---|---|---|---|
| CASCADE BOUNTY | 10.6c | 2.39c | 1.26a | 0.417c |
| Cascade Delight | 11.5ab | 2.75a | 1.33a | 0.630a |
| Meeker | 12.1a | 2.70ab | 0.85b | 0.459c |
| Willamette | 11.2bc | 2.52bc | 0.96b | 0.539b |

Analysis of three replications of 10 g of fruit.
Means within a column followed by the same letter are not significantly different at P ≦ 0.05, by Duncan's Multiple Range Test.

TABLE 8

Harvest comparison of BOUNTY with six Pacific Northwest raspberry cultivars, planted 1996 at Puyallup, Wash..

| | Yield (t/a) | Fruit weight (g) | Fruit Firm-ness (g) | Harvest season 5% | 50% | 95% | Length of season (d) |
|---|---|---|---|---|---|---|---|
| 1998 harvest | | | | | | | |
| CAS-CADE BOUNTY | 10.7a | 3.70a | 150a | 7/4a | 7/15a | 7/31a | 27a |
| Comox | 8.5ab | 3.59a | 195a | 6/27b | 7/9c | 7/20c | 23ab |

TABLE 8-continued

Harvest comparison of BOUNTY with six Pacific Northwest raspberry cultivars, planted 1996 at Puyallup, Wash..

| | Yield (t/a) | Fruit weight (g) | Fruit Firm-ness (g) | Harvest season 5% | 50% | 95% | Length of season (d) |
|---|---|---|---|---|---|---|---|
| Encore | 3.7b | 3.74a | 189a | 7/2ab | 7/10bc | 7/19c | 18b |
| Malahat | 9.1ab | 4.14a | 171a | 6/26b | 7/8c | 7/22c | 26ab |
| Meeker | 7.8ab | 3.30a | 165a | 7/2ab | 7/14ab | 7/29ab | 28a |
| Tulameen | 8.7ab | 4.17a | 159a | 7/2ab | 7/11bc | 7/25a-c | 23ab |
| Willa-mette | 7.2ab | 3.10a | 155a | 6/27b | 7/9c | 7/22bc | 25ab |
| 1999 harvest | | | | | | | |
| CAS-CADE BOUNTY | 7.9a | 3.10a | 160a | 7/5ab | 7/19a | 8/2a | 28a |
| Comox | 3.0ab | 2.94a | 239a | 7/8ab | 7/18ab | 7/29ab | 21a |
| Encore | 0.0b | — | — | — | — | — | — |
| Malahat | 0.0b | — | — | — | — | — | — |
| Meeker | 4.4ab | 3.34a | 172a | 7/11a | 7/22a | 8/1ab | 22a |
| Tulameen | 1.3ab | 3.64a | 166a | 7/7ab | 7/17ab | 7/28ab | 21a |
| Willa-mette | 2.2ab | 2.70a | 183a | 6/28b | 7/9b | 7/20b | 22a |

Based on the means of three replications of three plants for each location or harvest season.
Cultivars that died because of root rot had yield set to 0 and missing values for other variables.
Means within a column followed by the same letter are not significantly different at P ≦ 0.05, by Tukey's Studentized Range Test (HSD)

TABLE 9

Harvest comparison of BOUNTY with eight Pacific Northwest raspberry cultivars, planted 2000 at Puyallup, Wash.

| | Yield (t/a) | Fruit weight (g) | Fruit Firm-ness (g) | Harvest season 5% | 50% | 95% | Length of season (d) |
|---|---|---|---|---|---|---|---|
| 2003 harvest | | | | | | | |
| CAS-CADE BOUNTY | 11.7a | 3.3b | 163a | 7/30a | 8/10a | 8/25a | 25a |

TABLE 9-continued

Harvest comparison of BOUNTY with eight Pacific Northwest raspberry cultivars, planted 2000 at Puyallup, Wash.

| | Yield (t/a) | Fruit weight (g) | Fruit Firm-ness (g) | Harvest season 5% | 50% | 95% | Length of season (d) |
|---|---|---|---|---|---|---|---|
| Cascade Delight | 8.7b | 4.5a | 197a | 7/31a | 8/11a | 8/25a | 24a |
| Meeker | 1.2c | 3.2b | 174a | 8/1a | 8/11a | 8/19b | 18a |
| Chilliwack | 1.1c | 2.3b | 161a | 7/26a | 8/3b | 8/14c | 19a |
| Willa-mette | 0.4c | 1.9b | 124a | 7/25a | 8/4b | 8/12d | 18a |
| Cowichan | 0.0c | — | — | — | — | — | — |
| Malahat | 0.0c | — | — | — | — | — | — |
| Qualicum | 0.0c | — | — | — | — | — | — |
| Tulameen | 0.0c | — | — | — | — | — | — |
| 2004 harvest | | | | | | | |
| CAS-CADE BOUNTY | 15.2a | 3.5b | 144b | 7/21a | 8/3a | 8/18a | 28a |
| Cascade Delight | 8.7b | 4.2a | 223a | 7/23a | 8/1a | 8/15a | 22b |
| Meeker | 2.3c | 2.7bc | 173ab | 7/22a | 8/5a | 8/17a | 26ab |
| Chilliwack | 0.7c | 2.2c | 167ab | 7/18a | 7/24b | 8/7b | 20b |
| Cowichan | 0.0c | — | — | — | — | — | — |
| Malahat | 0.0c | — | — | — | — | — | — |
| Qualicum | 0.0c | — | — | — | — | — | — |
| Tulameen | 0.0c | — | — | — | — | — | — |
| Willa-mette | 0.0c | — | — | — | — | — | — |

Based on the means of three replications of three plants for each location or harvest season.
Cultivars that died because of root rot had yield set to 0 and missing values for other variables.
Means within a column followed by the same letter are not significantly different at P ≦ 0.05, by Tukey's Studentized Range Test (HSD)

I claim:

1. A new and distinct variety of raspberry plant, substantially as shown and described, characterized particularly by improved resistance to root rot.

* * * * *

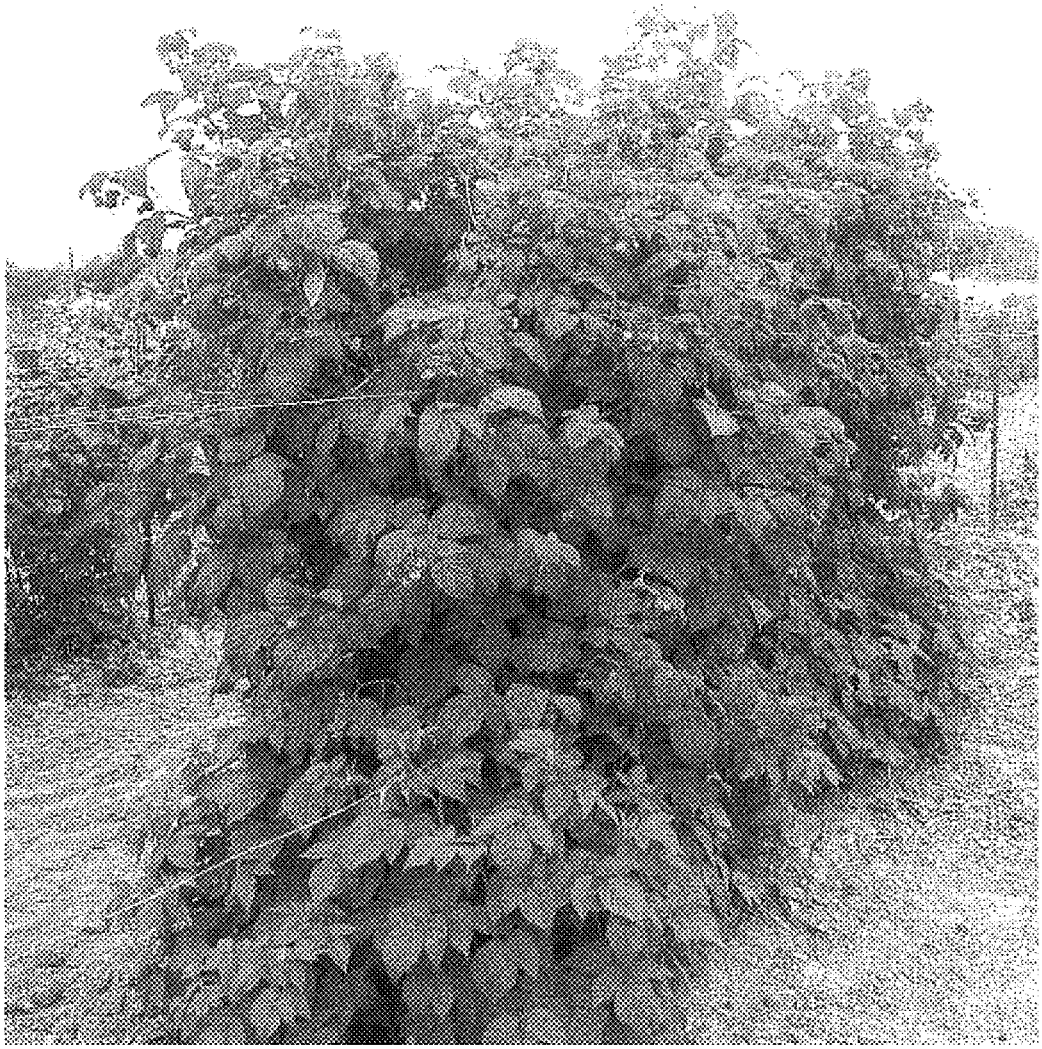
Figure 1. CASCADE BOUNTY, showing growth habit of the plant, June 23, 2004, Puyallup, Washington.

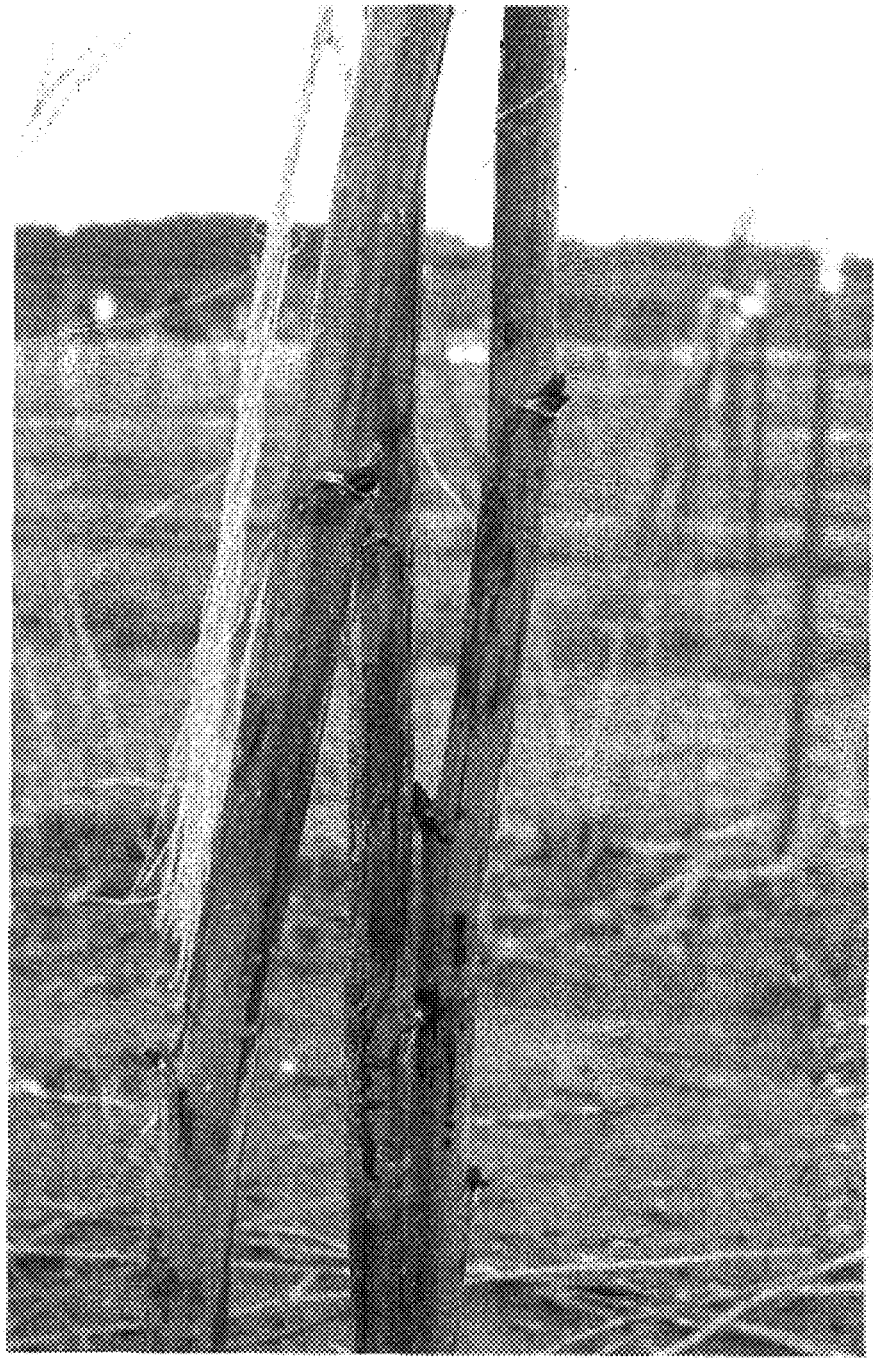
Figure 2. Winter cane of CASCADE BOUNTY with the waxy bloom rubbed off of a portion of the cane, February 3, 2004, Puyallup, Washington.

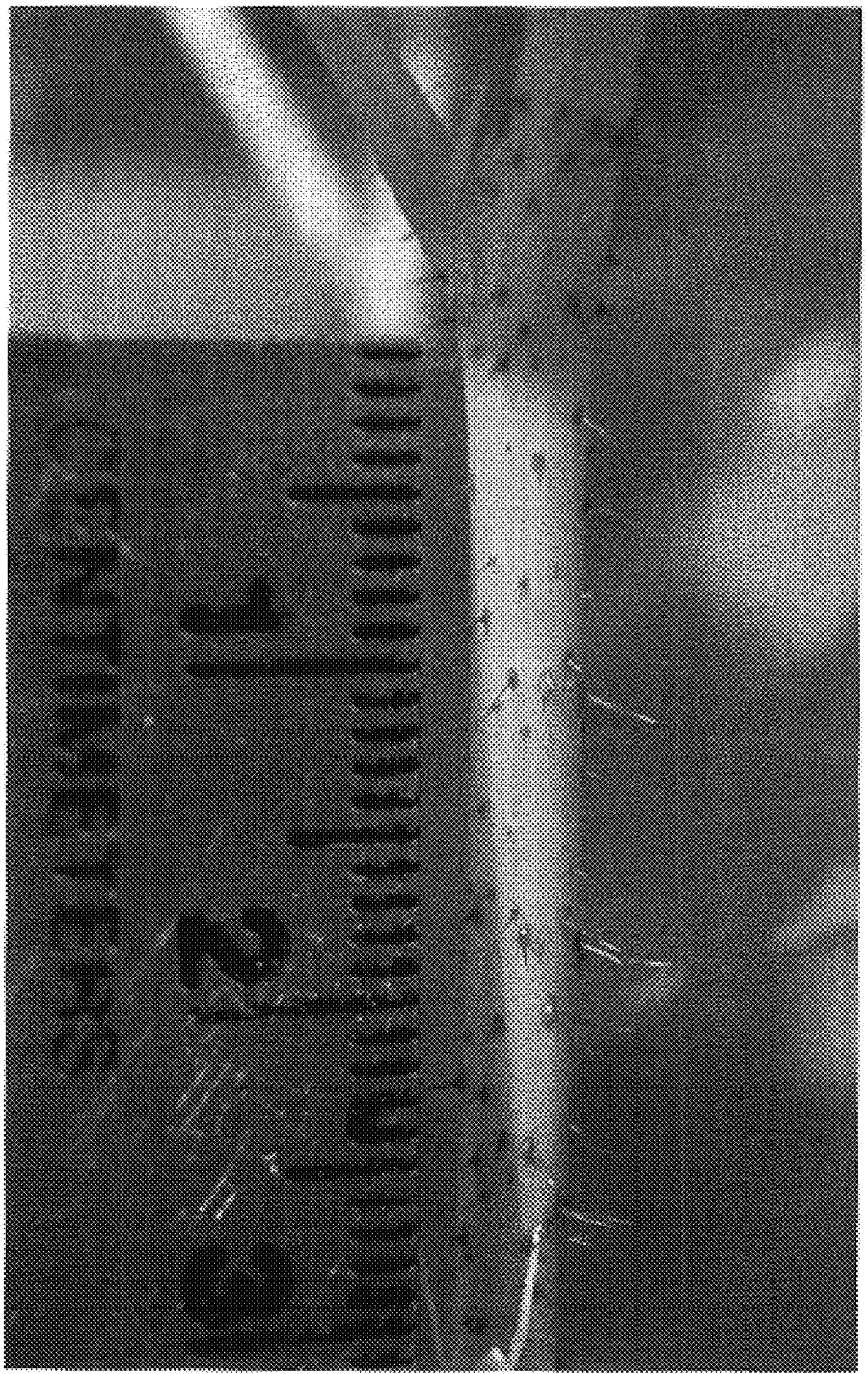
Figure 3. Young primocane of CASCADE BOUNTY less than 30 cm tall, grown in greenhouse, September 27, 2004, Puyallup, Washington.

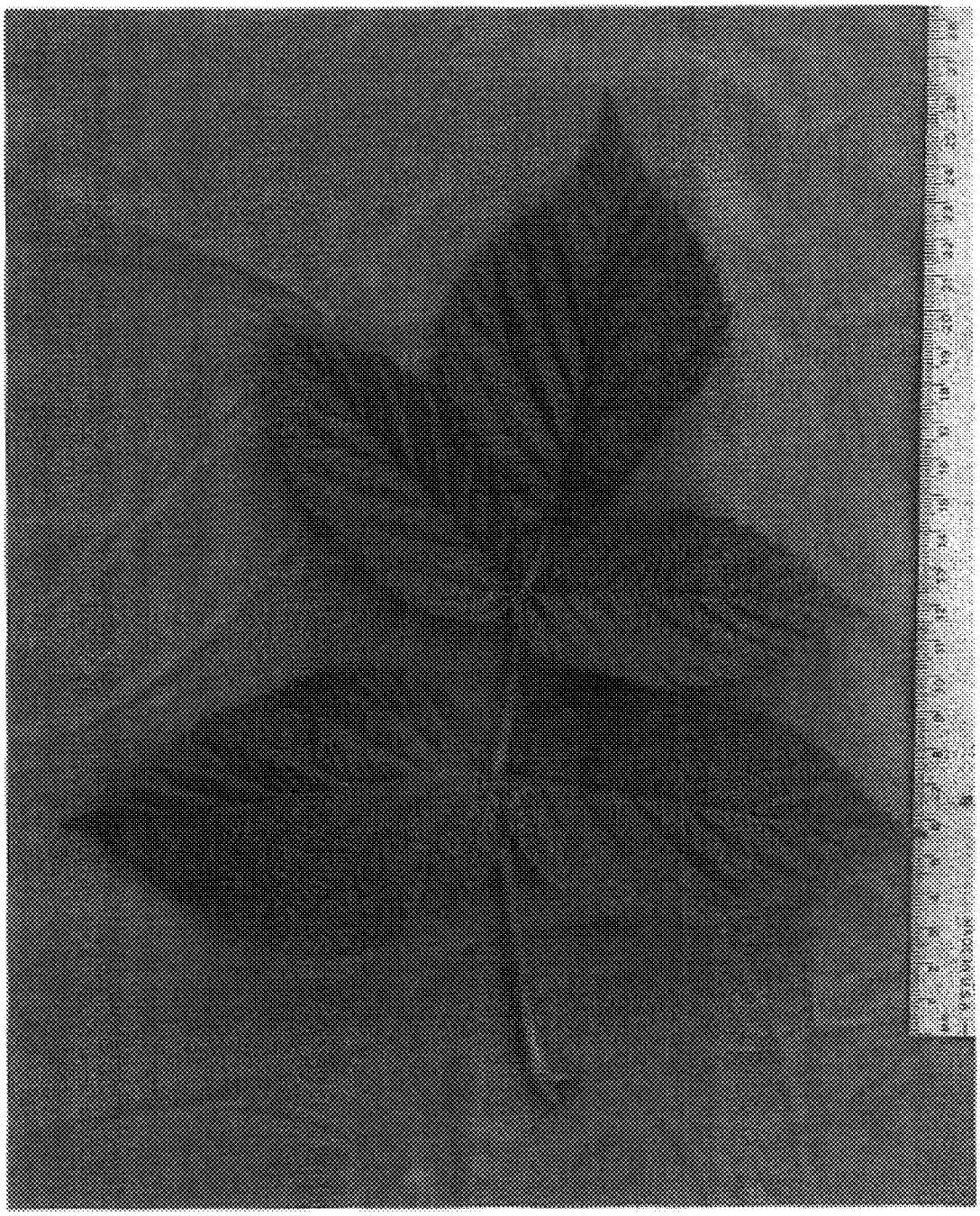
Figure 4. The upper surface of a leaf from a primocane of CASCADE BOUNTY, June 17, 2003, Puyallup, Washington.

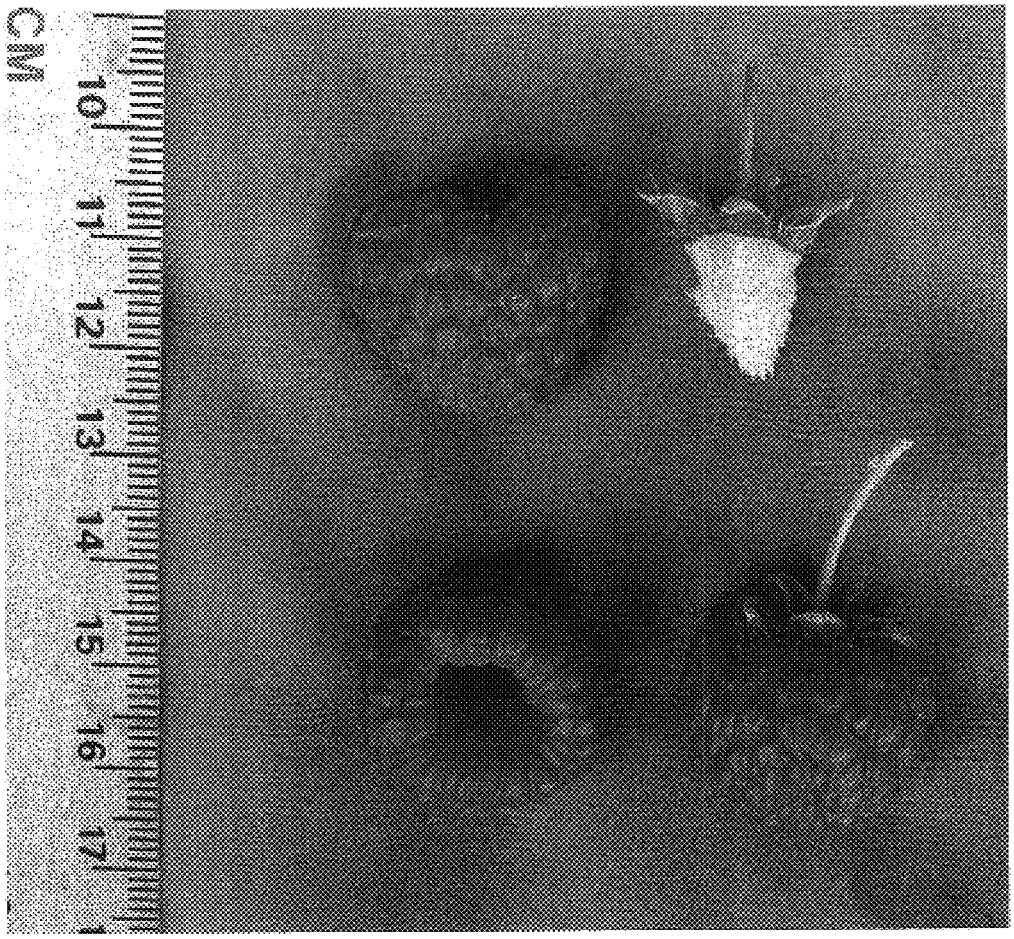
Figure 5. Fruit of CASCADE BOUNTY, July 7, 2004, Puyallup, Washington.